United States Patent [19]

Hoshi et al.

[11] Patent Number: 4,938,196
[45] Date of Patent: Jul. 3, 1990

[54] CONTROL DEVICE FOR HEATER FOR OXYGEN SENSOR OPERATIVE TO CORRECT TARGET RESISTANCE WITH REFERENCE TO STANDARD POWER SUPPLY THERETO

[75] Inventors: Kouichi Hoshi; Masaru Goudo; Mitsuhiro Suzuki; Ritsuo Masaki; Akira Hashizume; Hidemi Ohnaka, all of Susono, Japan

[73] Assignee: Toyota Jidosha Kabushiki Kaisha, Aichi, Japan

[21] Appl. No.: 413,231

[22] Filed: Sep. 27, 1989

[30] Foreign Application Priority Data

Oct. 7, 1988 [JP] Japan ............................ 63-132195[U]
Mar. 31, 1989 [JP] Japan .............................. 1-39007[U]
Jul. 27, 1989 [JP] Japan .............................. 1-88227[U]

[51] Int. Cl.$^5$ ............................................. F02D 41/14
[52] U.S. Cl. ..................................... 123/489; 204/425
[58] Field of Search ................ 123/489, 440; 204/425, 204/424, 406

[56] References Cited

U.S. PATENT DOCUMENTS

| 4,530,575 | 9/1985 | Chujo et al. | 123/440 |
| 4,543,176 | 9/1985 | Harada et al. | 123/489 |
| 4,561,402 | 12/1985 | Nakano et al. | 123/489 |
| 4,611,562 | 9/1986 | Nakano et al. | 123/489 |
| 4,655,182 | 4/1987 | Nakano et al. | 123/489 |
| 4,694,809 | 9/1987 | Nakano et al. | 123/489 |
| 4,708,777 | 11/1987 | Kuraoka | 123/440 |
| 4,715,343 | 12/1987 | Kinoshita | 123/489 |
| 4,721,084 | 1/1988 | Kawanabe et al. | 123/489 |
| 4,732,128 | 3/1988 | Yoshioka et al. | 123/489 |
| 4,873,642 | 10/1989 | Mieno et al. | 123/489 |

FOREIGN PATENT DOCUMENTS

| 0052649 | 3/1982 | Japan | 123/440 |
| 57-197459 | 12/1982 | Japan . | |
| 0224435 | 12/1984 | Japan | 123/440 |
| 60-164240 | 8/1985 | Japan . | |
| 60-202348 | 10/1985 | Japan . | |
| 61-35347 | 2/1986 | Japan . | |
| 63-302356 | 12/1988 | Japan . | |

Primary Examiner—Tony M. Argenbright
Assistant Examiner—Robert Mates
Attorney, Agent, or Firm—Kenyon & Kenyon

[57] ABSTRACT

For controlling supply of electric power to a heater for an oxygen sensor for detecting oxygen in an exhaust system of an internal combustion engine so as to maintain the electric resistance of the heater to a target value therefor, the target value is corrected based upon detection of the amount of electric power supplied to the heater so that difference between the detected amount of electric power supplied to the heater and a standard value therefor is cancelled.

10 Claims, 11 Drawing Sheets

CONTROL DEVICE FOR HEATER FOR OXYGEN SENSOR OPERATIVE TO CORRECT TARGET RESISTANCE WITH REFERENCE TO STANDARD POWER SUPPLY THERETO

BACKGROUND OF THE INVENTION

1. Field of the Invention

The present invention relates to an oxygen sensor to be mounted in an exhaust system of an internal combustion engine for the purpose of air/fuel ratio control of the engine, and more particularly, to a device for controlling temperature of such an oxygen sensor.

2. Description of the Prior Art

The oxygen sensor for detecting oxygen in the exhaust gases of an internal combustion engine is considered to be a device indispensable for controlling operation of the engine in a manner of accomplishing power up, fuel economy and exhaust gas purification. The oxygen sensor is generally made of a semi conductive material like a solid electrolyte, and provides an electrical output signal which changes in accordance with changes of oxygen density and also in accordance with changes of its temperature.

Figure 1:
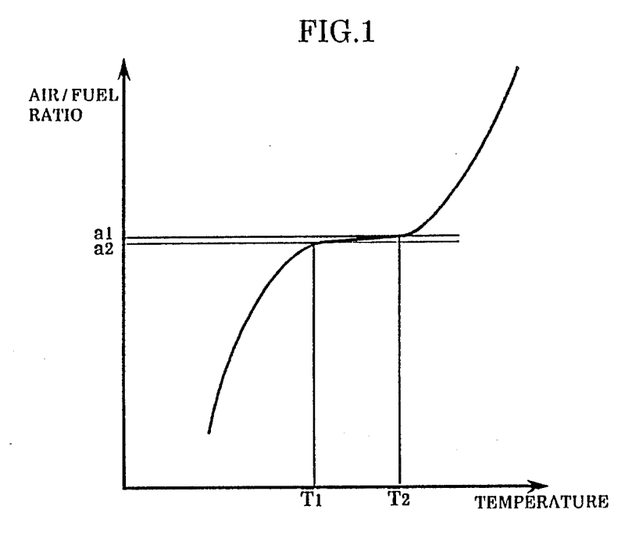
FIG. 1 is a graph showing a relation between the air/fuel ratio detectable by an oxygen sensor and the temperature thereof.

For example, the theoretical air/fuel ratio detectable by an oxygen sensor made of titanium dioxide according to whether oxygen exists or does not exist in the exhaust gases of an internal combustion engine changes in accordance with the temperature of the oxygen sensor as shown in FIG. 1. Therefore, if the oxygen sensor should detect air/fuel ratio in a range such as between $a_1$ and $a_2$, the temperature of the oxygen sensor must be controlled to be in a range such as between $T_1$ and $T_2$. Therefore, it is known to provide a heater for the oxygen sensor for controlling the temperature of the oxygen sensor. In the temperature control of the oxygen sensor by the heater the temperature of the oxygen sensor is surmised based upon measurement of the electric resistance of the heater, as described in, for example, Japanese Patent Laid-open Publication Nos. 57-197459, 61-35347, 60-202348 and 60-164240. The oxygen sensor is generally a small device having a small heat capacity, and therefore it changes its temperature readily according to the temperature, flow rate, etc. of the exhaust gases with which it is brought into contact. In view of these, it is also known to change electric power supplied to the heater in accordance with operating conditions of the internal combustion engine, as described in, for example, Japanese Patent Laid-open Publication Nos. 60-235050.

Figure 2:
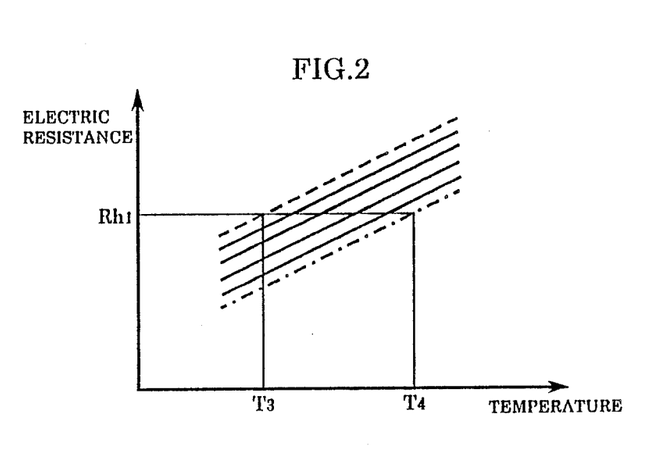
FIG. 2 is a graph showing a dispersion in the relation between the electric resistance and the temperature of a number of oxygen sensors manufactured according to a same design.

The above-mentioned conventional temperature control for the oxygen sensor is based upon the fundamental physical phenomenon that the electric resistance of an electric heater changes in accordance with the temperature thereof. However, the value of electric resistance of the heater incorporated in the oxygen sensor is different within an allowable range of error according to each commercial product. As shown in FIG. 2, although each oxygen sensor of the same design shows a certain determinate rate of change of electric resistance relative to the change of temperature, the absolute value of the temperature at which each oxygen sensor has a certain electric resistance such as $Rh_1$ differs relatively widely so as to be $T_3$-$T_4$ so that the performance lines for the same products distribute within an upper limit shown by a broken line and a lower limit shown by a dot and dash line.

SUMMARY OF THE INVENTION

In view of the above-mentioned problem in the temperature control of the oxygen sensor caused by the dispersion in the values of electric resistance of the heater it is the object of the present invention to provide an improved control device for controlling supply of electric power to the heater of the oxygen sensor which can resolve the above-mentioned problem.

According to the present invention, the above-mentioned object is accomplished by a control device for controlling supply of electric power to a heater for an oxygen sensor for detecting oxygen in an exhaust system of an internal combustion engine for a vehicle, said control device comprising a means for detecting electric resistance of said heater and controlling said supply of electric power so as to maintain the detected electric resistance at a target value therefor, further comprising a means for detecting a predetermined operating condition of the engine, a means for detecting the amount of electric power supplied to said heater when the engine is operating at said predetermined operating condition, and a means for modifying said target value for the electric resistance of said heater so as to cancel difference between said detected value of said supply of electric power to said heater and a standard value therefor.

The temperature of an oxygen sensor mounted in an exhaust system of an internal combustion engine so as to be exposed to the flow of exhaust gases therein for detecting oxygen density of the exhaust gases with incorporation of a heater for controlling the temperature thereof is determined according to the balance between the amount of heat supplied thereto by the heater and the amount of heat dissipated therefrom by heat conduction through the mechanical supporting structure for the sensor, heat convection due to contact with the exhaust gases and hear radiation to the environment. With respect to a number of oxygen sensors manufactured according to the same design, it is expected that the dispersion in the mechanical shape and dimensions of the products which determine the dissipation of heat therefrom by the above-mentioned heat conduction, heat convection and heat radiation is much smaller than that in the value of electric resistance of the heater incorporated therein. Therefore, it is expected that when each oxygen sensor manufactured according to the same design is assembled into an internal combustion engine of the same design, if the same amount of heat is supplied to the oxygen sensor by the heater under the same operating condition of the engine, all of the oxygen sensors will attain the same temperature condition.

Figure 3:
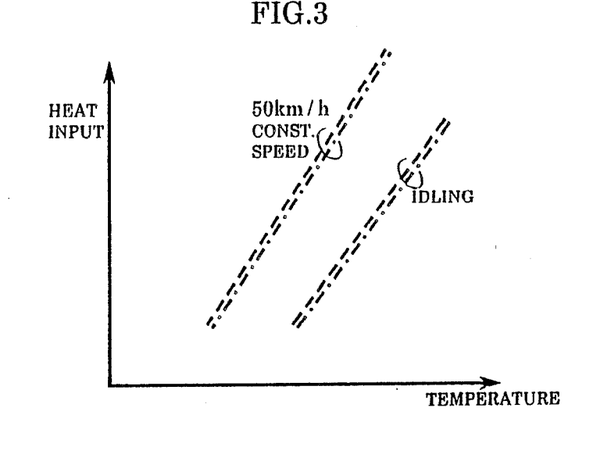
FIG. 3 is a graph showing a relation between the heat input and the temperature of a number of oxygen sensors manufactured according to the same design.

In fact, this is true. According to the test results obtained by assembling a number of oxygen sensors of the same design into an internal combustion engine mounted in an automobile the relation between the electric power supplied by the heater and the temperature of the oxygen sensor is as shown in FIG. 3 for the constant speed running at 50 km/h and for the idling, wherein the broken lines showing the upper limit performance and the dot and dash lines showing the lower limit performance in the respective operating conditions substantially accorded with one another.

Therefore, if the discrepancy in the value of electric resistance of the heater in each oxygen sensor available as a commercial product from a certain design target value therefor is confirmed under the supply of a certain standard electric power thereto under a predetermined operating condition of the engine, and if the target value for the electric resistance of the heater for the temperature control of the oxygen sensor is modified according to the thus confirmed discrepancy, it is possible to control correctly the temperature of the oxygen sensor by the conventional manner of control of detecting the electric resistance of the heater and controlling the supply of electric power to the heater so as to let the detected value of the electric resistance to the modified target value, without being affected by the dispersion in the value of the electric resistance of the heater in each product. If the modification of the target value for the electric resistance of the heater is automatically carried out with respect to each product in the actual operation thereof according to the so called learning control, the quality control in the production of the heaters may be substantially relaxed.

According to an embodiment of the present invention, said means for detecting the electric resistance of said heater and said means for detecting the amount of electric power supplied to said heater may include a common series connection of a switching transistor and a comparing resistor connected in series with said heater, and a means for measuring a voltage across said comparing resistor, said switching transistor being controlled to be conductive according to a controlled duty factor.

The above-mentioned means for detecting the amount of electric power supplied to said heater may collect data of the amount of electric power applied to said heater cyclically for a predetermined period and determine the amount of electric power supplied to said heater as a mean value of said data.

Further, the above-mentioned means for detecting the amount of electric power supplied to said heater may start to detect the amount of electric power supplied to said heater when the engine is operating at said predetermined operating condition for a predetermined period.

Further, the above-mentioned means for detecting the amount of electric power supplied to said heater may detect the amount of electric power supplied to said heater when the engine is operating at said predetermined operating condition just after the engine has been operating at a predetermined pro-operating condition. Such a pro-operating condition may be that the vehicle has been running at a speed within a predetermined normal speed range for a predetermined period, that the engine has been operating at load and rotational speed correlated within a predetermined mutually balanced range, or that a mean value of the amount of intake air in a predetermined period is in a predetermined medium range.

Further, the above-mentioned means for detecting the amount of electric power supplied to said heater may collect data of the amount of electric power supplied to said heater for a period which is equal to or longer than a predetermined minimum period but is not longer than a predetermined maximum period during which the engine is operating at said predetermined operational condition, and provide the amount of electric power applied to said heater as a mean value of said data.

BRIEF DESCRIPTION OF THE DRAWING

In the accompanying drawings.

DESCRIPTION OF THE PREFERRED EMBODIMENTS

In the following the invention will be described in more detail with respect to some preferred embodiments thereof with reference to the accompanying drawings.

Figure 4:
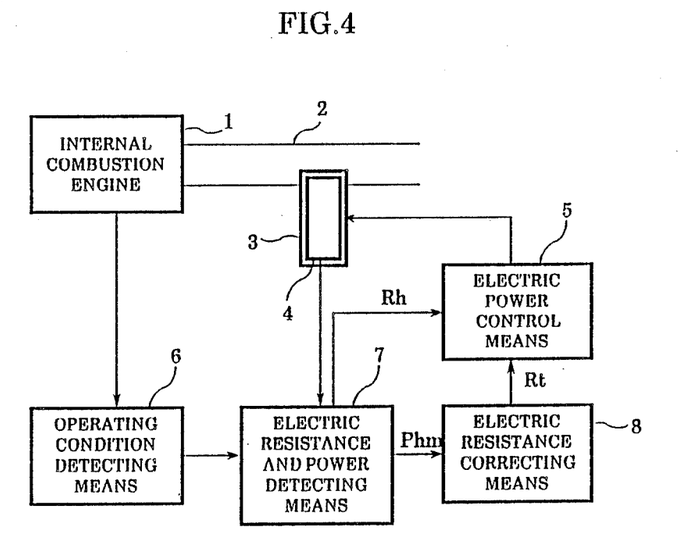
FIG. 4 is a diagram showing a general construction of the control device for controlling supply of electric power to the heater for the oxygen sensor according to the present invention.

Referring to FIG. 4 showing the overall construction of the control device for controlling supply of electric power to the heater for the oxygen sensor, an engine 1 schematically shown by a block discharges exhaust gases through an exhaust passage 2, and an oxygen sensor 3 which is also schematically shown by a block is adapted to detect oxygen included in the exhaust gases flowing through the exhaust passage 2. The oxygen sensor 3 is provided with a heater 4 also schematically shown by a block. The heater 4 is supplied with a controlled electric power from an electric power control means 5 which will be described in more detail hereinunder.

A predetermined operating condition of the engine 1 is detected by an operating condition detecting means 6 which will also be described in more detail hereinunder. The predetermined engine operating condition herein referred to may be any optional operating condition. However, it is desirable that such an operating condition that will generally continue for a relatively long period like the idling or a constant speed running at a speed around 50 km/h, is selected for the predetermined operating condition. When it was detected by the operating condition detecting means 6 that the engine is operating at the predetermined operating condition, a signal is dispatched from the operating condition detecting means 6 to the electric resistance and power detecting means 7 which then calculates the amount of electric power supplied to the heater 3, and dispatches a signal showing a mean value Phm of the electric power supplied to the heater to an electric resistance correcting means 8 as described in more detail hereinunder.

The electric resistance correcting means 8 calculates a correction amount for the target value for the electric resistance of the heater based upon the difference between the mean value Phm of the electric power supplied to the heater and a standard value therefor in accordance with a function map stored therein and calculates a target value Rt for the electric resistance of the heater, and then dispatches a signal showing the target value Rt to the electric power control means 5.

The electric power control means 5 compares the value of electric resistance Rh of the heater 4 detected by the electric resistance and power detecting means 7 with the target value Rt therefor and supplies a controlled electric power to the heater 4 so as to let Rh be accorded with Rt.

Figure 5:
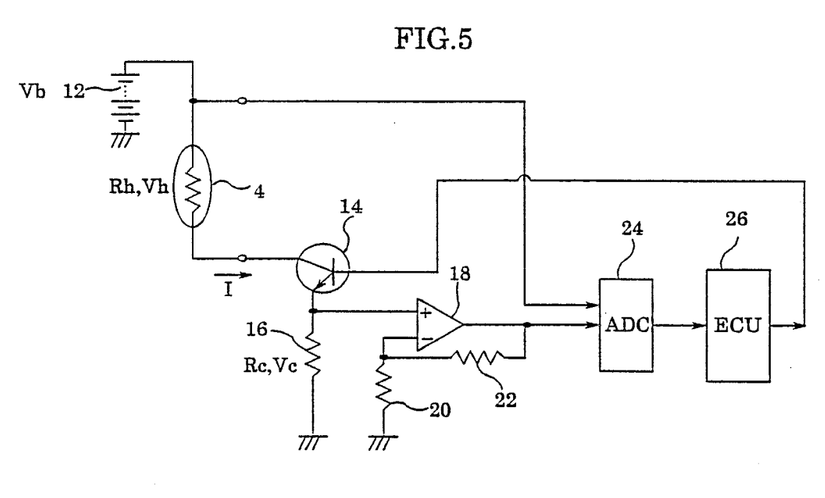
FIG. 5 is an electric circuit diagram showing an embodiment of the control device for the heater for the oxygen sensor according to the present invention.

FIG. 5 shows an embodiment of the electric circuit which provides the electric resistance and power detecting means 7, the electric resistance correcting means 8 and the electric power control means 5 diagrammatically shown in FIG. 4 in the form of a combination with the heater 4. The heater 4 is connected in series with a switching transistor 14 and a comparing resistor 16 to be powered by a battery 12 of a vehicle. The voltage Vc generated in the comparing resistor 16 is amplified by an amplifier circuit constructed by an operational amplifier 18 and resistors 20 and 22 to be amplified e.g. about ten times, is processed through an A/D converter (ADC) 24, and is supplied to an electronic control unit (ECU) 26. The voltage Vb of the battery 12 is also processed through the A/D converter 24 and is input to the electronic control unit 26.

Figure 6:
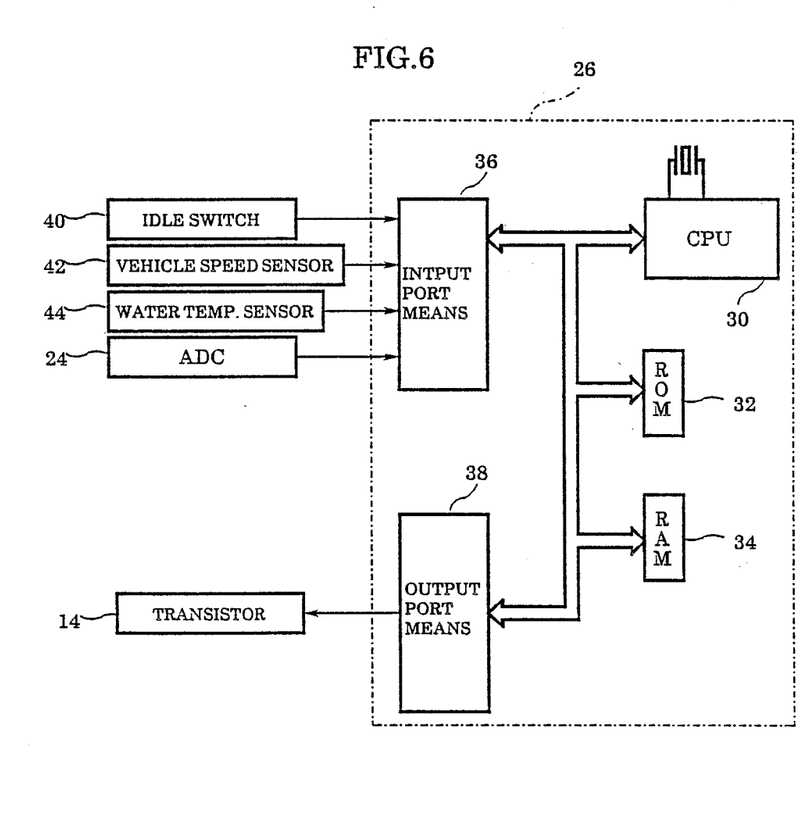
FIG. 6 is a block diagram showing a general construction of the electronic control circuit included in the electric circuit diagram shown in FIG. 5.

The electronic control unit 26 is a microcomputer which itself is well known in the art and diagrammatically shown in FIG. 6, including a central processing unit (CPU) 30, a read only memory (ROM) 32, a random access memory (RAM) 34, an input port means 36 and an output port means 38. An idle switch 40 for detecting a throttle valve provided in an intake system (both not shown) of the internal combustion engine being closed to its idling position, a vehicle speed sensor 42 for detecting running speed of the vehicle carrying this control system, a water temperature sensor 44 for detecting temperature of the cooling water in the internal combustion engine, and the afore-mentioned A/D converter 24 supply respective input signals to the electronic control unit 26 through the input port means 36. The electronic control unit 26 outputs a signal for putting on and off the transistor 14 through the output port means 38.

Figure 7:
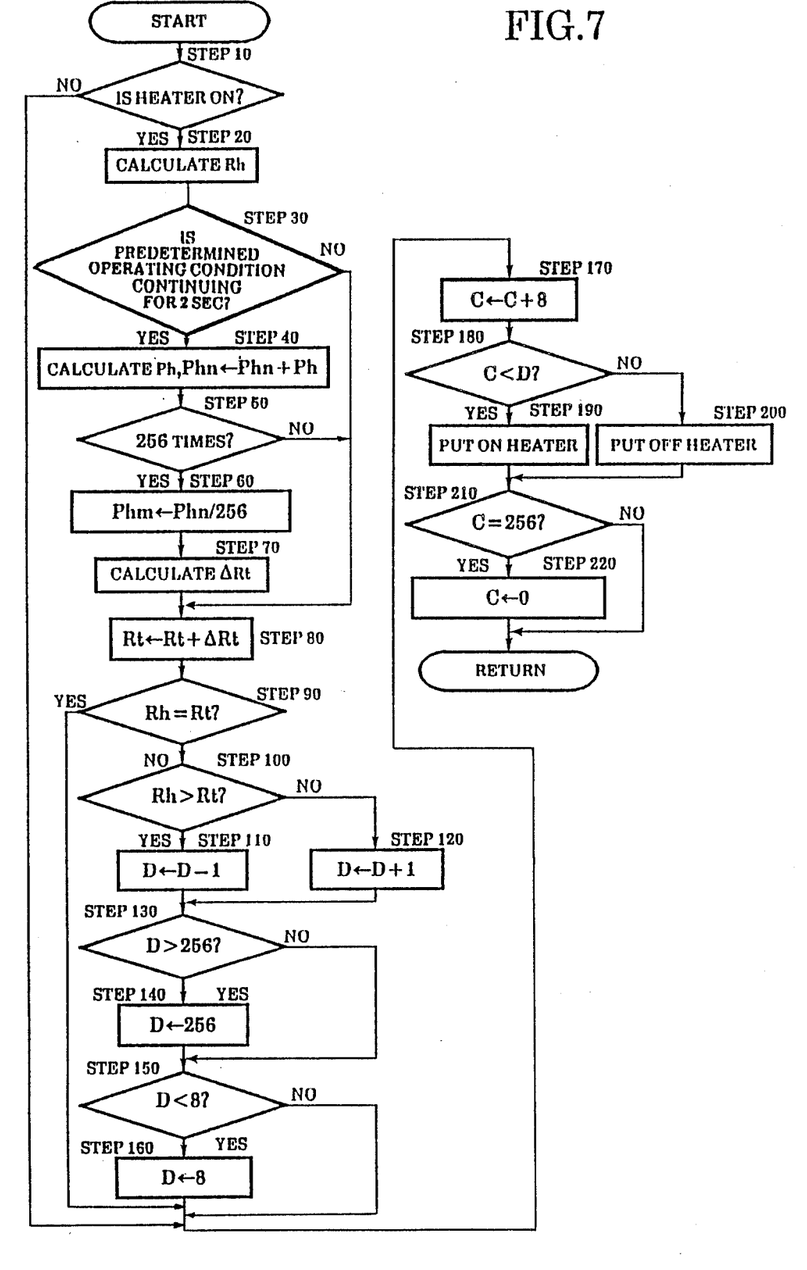
FIG. 7 is a flow chart showing the operation of an embodiment of the control device for the heater for the oxygen sensor according to the present invention.

In the following the operation of the control device for the heater for the oxygen sensor according to the present invention shown in FIGS. 4-6 will be described in accordance with the flow chart shown in FIG. 7. In the present invention the control routine according to the flow chart shown in FIG. 7 is repeated at a cycle time of 16 ms.

After start, in step 10 it is checked if the heater is on or not. If the answer is yes, the control process proceeds to step 20, and the electric resistance of the heater Rh is calculated based upon the voltage Vb of the battery 12, the voltage Vc of the comparing resistor 16 and the resistance Rc of the comparing resistor 16 according to the following formula:

$Rh = (Vb/Vc - 1) \cdot Rc$

Then the control process proceeds to step 30.

In step 30 it is checked if the engine is operating at a predetermined operating condition continuously for 2 seconds. The predetermined operating condition of the engine may be, for example, such an idling condition that the idle switch 40 is on, the vehicle speed detected by the vehicle speed sensor 42 is lower than 5 km/h, and the temperature of the cooling water in the engine detected by the water temperature sensor 44 is higher than 70° C. When the condition for this step is satisfied, the process proceeds to step 40, and the value of electric power Ph supplied to the heater is calculated according to the following formula:

$Ph = \{Vc \cdot (Vb - Vc)/Rc\} \cdot (D/256)$

Herein "D" is a count number corresponding to the duty ratio in a pulse-like supply of electric power to the heater as described hereinunder. Each newly calculated Phn is added to the value Phn in the memory therefor. The value of Phn is reset to zero at the starting of the control routine. Then, the control process proceeds to step 50.

In step 50 it is checked if this step has been passed 256 times. If the answer is yes the process proceeds to step 60.

In step 60 the value Phn in the memory is divided by 256 so as to calculate a mean value Phm of the value of electric power Ph. Then the process proceeds to step 70.

Figure 8:
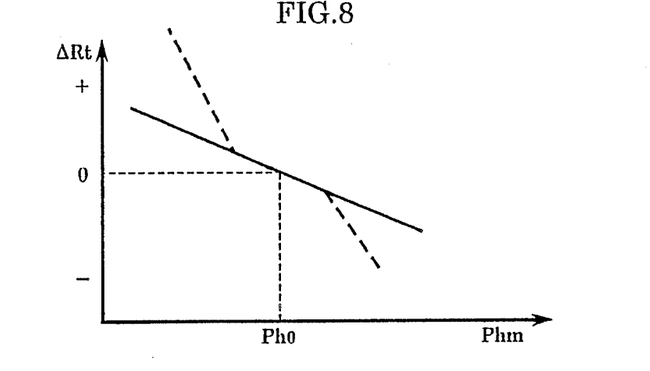
FIG. 8 is a graph showing a relation between the difference in the electric power supplied to the heater from the standard value therefor and the correction for the target value for the electric resistance of the heater.

In step 70 a correction amount ΔRt is obtained based upon the mean value Phm of the electric power supplied to the heater in accordance with a function map stored in the ROM 32 and as exemplarily shown in FIG. 8 which provides the correction amount ΔRt for the target value Rt for the electric resistance of the heater corresponding to the difference of Phm from the standard value Pho for the electric power to be supplied to the heater. As shown in FIG. 8 ΔRt is made to be a larger negative value as Phm is larger than Pho. Thus, as the electric power supply to the heater is larger than the standard value, the target value for the electric resistance of the heater is lowered so that the over supply of electric power is corrected. The ratio of change of ΔRt relative to Phm may be a relatively small negative value as shown by the solid line in FIG. 8 only in a region closely around Pho, and the changing ratio may be decreased so as to be a greater negative value as shown by broken lines in the figure when Phm is much different from Pho. Further, the changing ratio in the region where the Phm is much smaller than Pho may be more decreased so as to be a further greater negative value than that in the range where Phm is much larger than Pho, so that the deficit in the heat supply is quickly recovered. Then the process proceeds to step 80.

In step 80 the currently employed target value Rt for the electric resistance of the heater is corrected by the correction amount ΔRt being added thereto so that the target value Rt is renewed. Then the process proceeds to step 90.

In step 90 it is checked if Rh calculated at each pass through step 20 is equal to Rt, and if the answer is no the process proceeds to step 100. In step 100 it is checked if Rh is greater than Rt, and if the answer is yes, the process proceeds to step 110, whereas if the answer is no the process proceeds to step 120. In step 110 the value D in the duty counter is decreased by one, whereas in step 120 the value D in the duty counter is increased by one. The value D in the duty counter is a count number corresponding to the duty ratio in the pulse-like supply of electric power to the heater, and is a count value which provides the duty ratio of a period in which a pulse-like electric current is supplied to the heater when it is divided by 256. This count value is controlled not to be less than 8 for the convenience of control in the actual operation. Therefore, the duty ratio is changed in a range of 3.125–100%. The process for restricting the value of D in the range of 8–256 is carried out in steps 130–160. In more detail, in step 130 it is checked if D is larger than 256, and if the answer is yes the process proceeds to step 140, and the value of D is set to 256. Further, in step 150 it is checked if the value of D is less than 8 or not, and if D is less than 8, the process proceeds to step 160, and the value of D is set to 8. Then the process proceeds to step 170. If the answer in step 150 is no, the process proceeds to step 170.

Returning to steps 10 and 90, if it was judged that the heater is not on in step 10, or if it was judged that Rh is equal to Rt in step 90, the process immediately proceeds to step 170.

Figure 9:
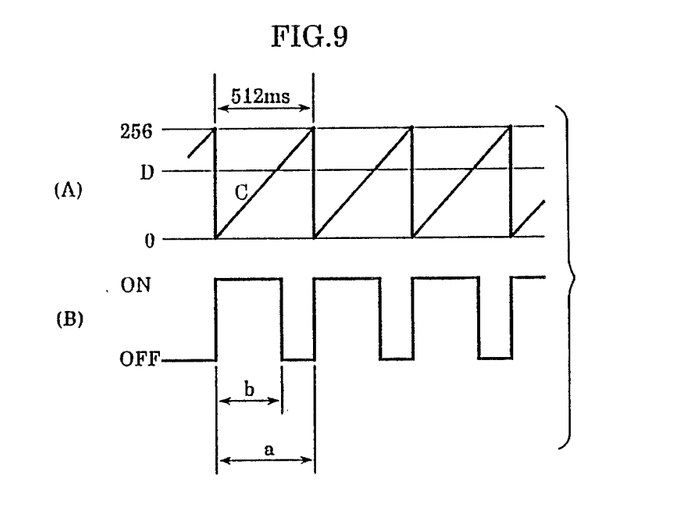
FIGS. 9(A) and 9(B) are a graph showing a manner of the duty ratio control for the electric power supplied to the heater carried out in the latter half steps of the flow chart shown in FIG. 7.

In step 170 the value of flow count C is compared with the value of the duty count D. The flow count C is a count value which is increased by 8 every time when the control process passes this step at the repetition cycle of 16 ms, and is reset to zero when it has reached 256. Since the control process is repeated at the cycle time of 16 ms, by the flow count C being increased by 8 every time when the control process passes this flow routine, the flow count C will reach 256 at each 512 ms. This condition is shown in FIG. 9, part (A), wherein an example of the duty count D is also shown. When the temperature control for the heater for the oxygen sensor is normally carried out according to a predetermined condition, the value of the duty count D determined based Phm calculated in step 60 will be maintained at a value intermediate between 0 and 256 as shown in FIG. 9, part (A).

As long as it is judged in step 180 that the value of C is smaller than that of D, the control process proceeds to step 190, and the heater is kept at on condition. By contrast, if it was judged in step 180 that the value of C is equal to or greater than that of D, the process proceeds to step 200, and the heater is put off. This operation is shown in FIG. 9, part (B) to correspond to the diagram of part (A). Thus, the electric current supplied to the heater is a pulse-like current, in which the ratio of the period "b" during which the heater is put on to the cycle period "a" is the duty ratio of the pulse-like electric current which is determined by the value of the duty count D.

When it was judged in step 210 that the flow count C has reached 256, the process proceeds to step 220, and the flow count C is reset to zero. When it was judged in step 210 that the value of flow count C has not yet reached 256, the control process is recirculated.

As is understood from steps 30–70 the correction amount for the target value for the electric resistance of the heater is calculated as a mean value of 256 values obtained at an interval of 16 ms by selecting a time when the engine is operating at the predetermined operating condition continuously for more than 2 seconds. Therefore, it is avoided that any momentary change of the operating condition of the engine affects the temperature control of the heater. However, the combination of the circle time 16 ms and the count number 256 is only a preferred embodiment, and of course the present invention is not limited to such a combination. The circle time 512 ms for the flow count C is also only a preferred embodiment.

Figure 10:
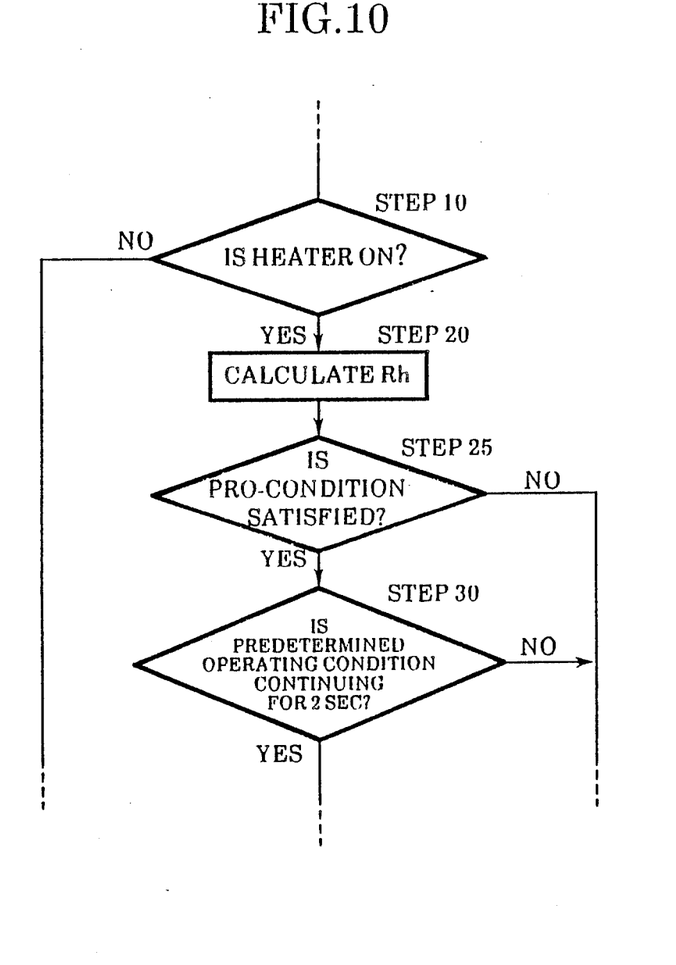
FIG. 10 is a partial view of the flow chart showing a modification to be incorporated at a part of the flow chart shown in FIG. 7.

In the embodiment according to the flow chart shown in FIG. 7, when it was judged in step 30 that the predetermined operating condition of the engine is continuing for 2 seconds, the data for renewing the target value for the electric resistance of the heater are collected. However, it will be effective for accomplishing a more improved temperature control for the oxygen sensor in spite of various changes of the operating conditions of the engine to consider through what operating conditions the vehicle has come to the current operating condition. For example, if the engine has been operating at very high load and rotational speed until immediately before the current instant, the temperature of the oxygen sensor will be relatively high and it will take a substantial time for the oxygen sensor to cool down to a normal temperature condition. In such a case it will be desirable that the temperature of the oxygen sensor is controlled according to the target value for the electric resistance which is not affected by such operating conditions outside a standard operating condition. FIG. 10 shows a modification for the temperature control of the oxygen sensor according to the present invention in which the history of operation prior to the current condition is considered. FIG. 10 shows only a part of the flow chart around the step 30 of the flow chart shown in FIG. 7 to show the modification while avoiding duplication of the illustration.

In the embodiment shown in FIG. 10, prior to the step 30 for checking if the predetermined operating condition is continuing for 2 seconds, in step 25 it is checked if the engine was operating at a predetermined pro-operating condition immediately preceding the current state. The pro-operating condition to be checked in step 25 are, for example, as follows:

(a) Conditions with regard to vehicle speed

It is checked if the vehicle speed has been maintained in a normal speed range such as, for example, 30–100 km/h continuously for a predetermined period such as, for example, 10 seconds, and if the answer is yes, the control process proceeds to step 30, whereas if the answer is no, the control process proceeds from step 25 to step 80. Herein such a lower limit for the vehicle speed is incorporated in consideration of the possibility that the engine is substantially heated up in the slow running of the vehicle as in the traffic jam.

Figure 11:
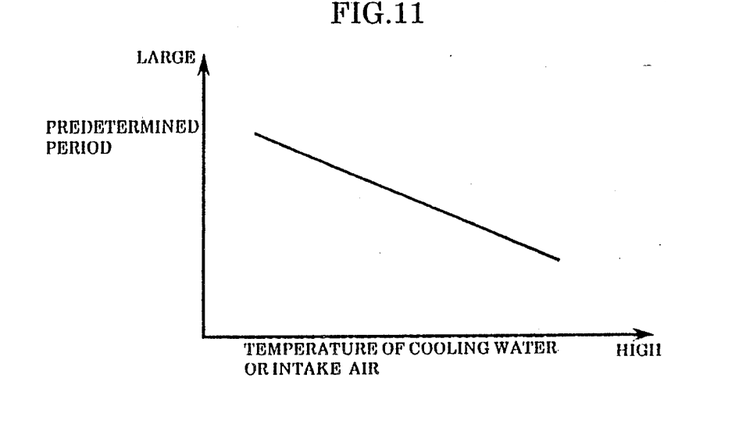
FIGS. 11–14 are graphs showing several possibilities for the conditions employable as the pro-operating condition in the step 25 according to the modification of the flow chart shown in FIG. 10.

The pro-condition with regard to the vehicle speed may be modified as shown in FIG. 11, in consideration of the purpose of introducing such a condition into the temperature control of the oxygen sensor, so that the predetermined period is shortened as the cooling water temperature of the engine or the engine intake air temperature based upon atmospheric temperature is higher.

Figure 12:
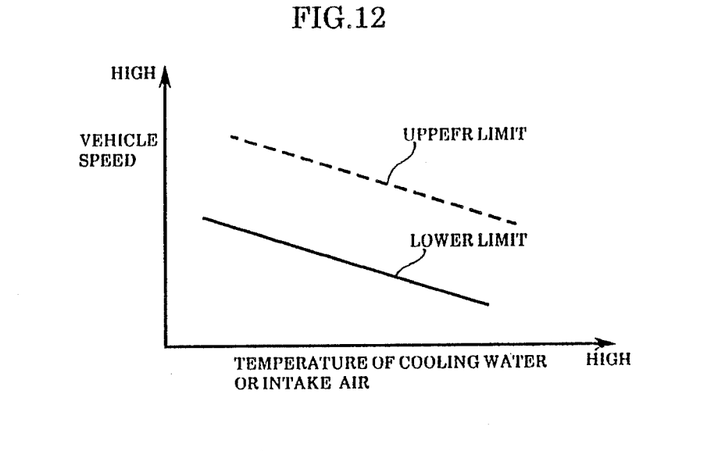

Similarly, as shown in FIG. 12 the range of the normal vehicle speed may be modified to be lower as the cooling water temperature of the engine or the engine intake air temperature based upon atmospheric temperature is higher.

(b) Condition with regard to engine load

Figure 13:
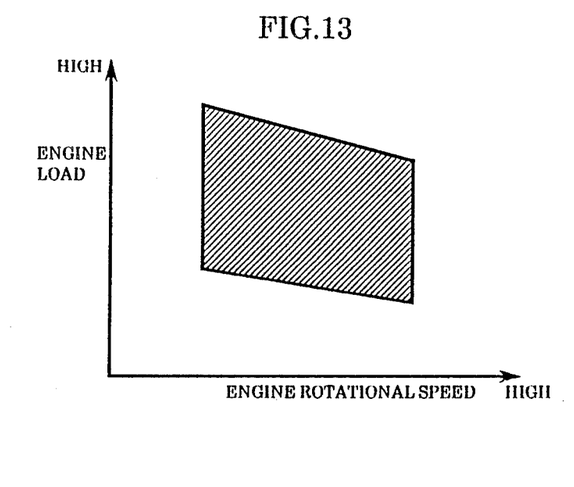

The pro-operating condition to be judged in step 25 may be the condition that the relation between the rotational speed and the load of the engine has been within a range such as shown by hatching in FIG. 13 for more than a predetermined period. If this condition is satisfied, the control process may proceed to step 30. The load of the engine may be replaced by corresponding intake air flow or intake vacuum.

(c) Condition with regard to integration of intake air

Figure 14:
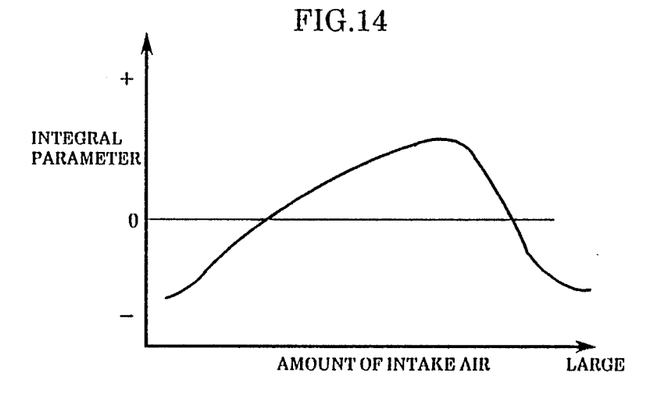

First, a concept such as "integration parameter" is determined relative to the amount of intake air as shown in FIG. 14. Then, the value of the integration parameter at each lapse of cycle time corresponding to the amount of intake air at each instant is integrated to obtain an integration value. In step 25 it is checked if the above integration value is greater than a predetermined value, and when the answer is yes, the control process proceeds to step 30, whereas if the answer is no, the process proceeds to step 80. The fact that the above integration value is greater than a predetermined value means that the engine has been operating continuously for a predetermined period at a medium load with a medium supply of intake air. By carrying out the correction of the target value for the electric resistance of the heater when and only when the engine has been operating for a predetermined period at a medium load and is now in the predetermined operating condition as detected in step 30, a more stable correction of the target value for the electric resistance of the heater is available.

The above conditions (a)-(c) may be employed as appropriately combined with one another. When the correction of the target value for the electric resistance of the heater is carried out only when some of those pro-conditions are satisfied, the electric resistance of the heater will be controlled to provide a more stabilized performance.

In the above descriptions of the operation of the embodiments of the control device for the heater for the oxygen sensor according to the present invention in reference to FIG. 7 it was assumed that the control routine according to the flow chart in FIG. 7 is repeated with a cycle time of 16 ms and the renewal of the target value for the electric resistance of the heater is carried out based upon the mean value of the electric power supplied to the heater calculated as a result of 256 times measurements thereof under the condition that a predetermined operating condition is contunuing for 2 seconds. This means that therefore the target value for the electric resistance of the heater is renewed based upon the mean value of the electric power supplied to the heater over a period of 4096 ms. It is desirable for the improvement of the accuracy of measurement to depend upon a mean value of as large a number of measurements as possible in obtaining the value of the supply of electric power to the heater if the operating condition of the vehicle is stabilized for a sufficiently long period. However, when the vehicle is operated with violent changes of operating conditions, if the number of measurement is large, the opportunity of obtaining the mean value after the completion of the predetermined number of measurements decreases, and therefore the processes especially prepared for the renewal of the target value for the electric resistance of the heater will be carried out at too small frequency, and the desirable maintenance of the target value for the electric resistance of the heater will be obstructed because of insufficiency of learning.

Figure 15:
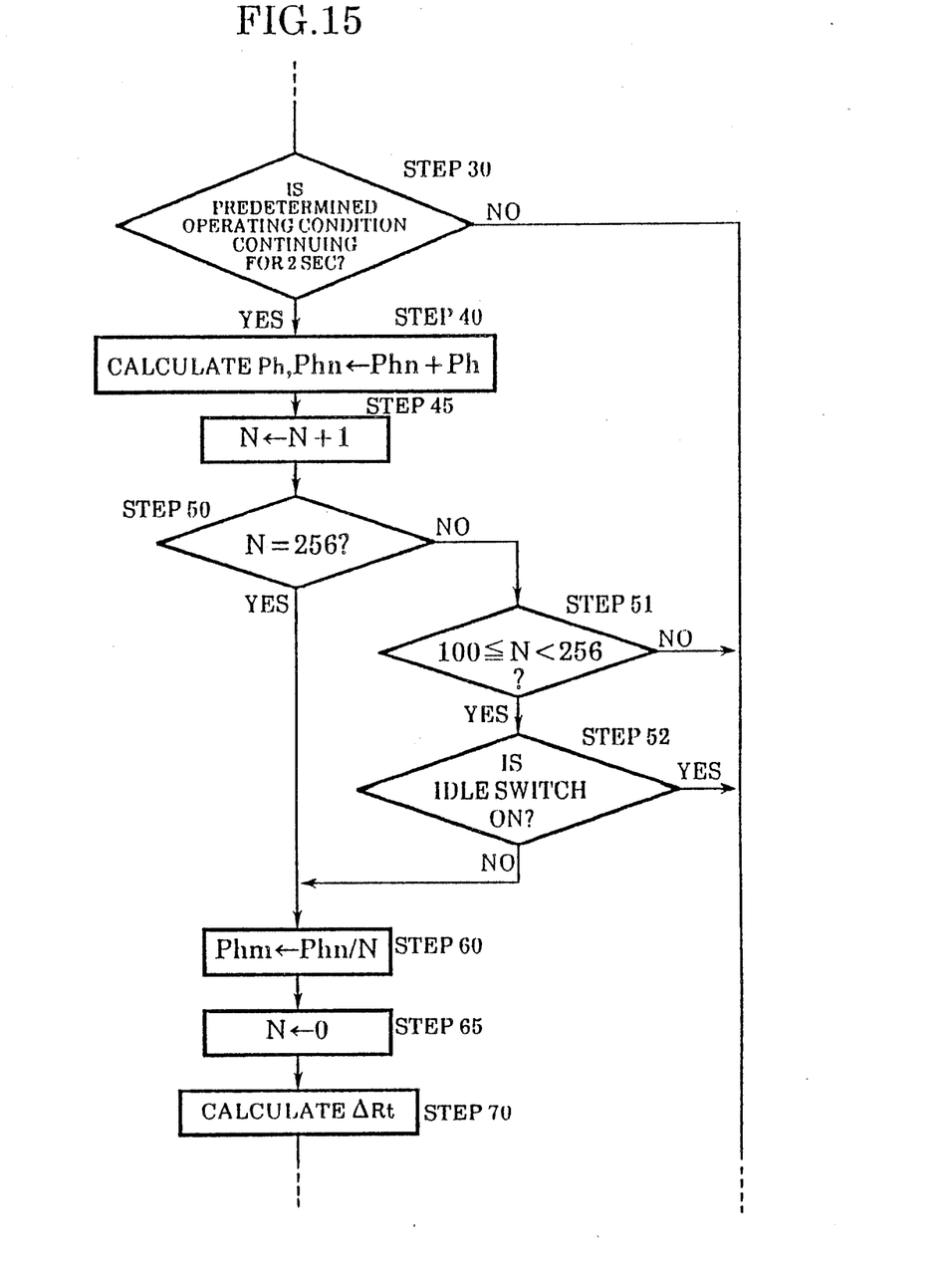
FIG. 15 is a partial view of the flow chart showing another modification employable at a part of the flow chart shown in FIG. 7.

FIG. 15 is a part of the flow chart showing processes for a partial modification of the flow chart shown in FIG. 7 to meet with the above-mentioned problem. The processes shown in FIG. 15 are a modification about the steps 30–70 in the flow chart of FIG. 7. According to this modification, the predetermined operating condition checked in step 30 is particularly an idling condition, and a parameter for judging the idling condition is that an idle switch such as the switch 40 in FIG. 6 is put on. When it was judged in step 30 that the predetermined operating condition is continuing for 2 seconds, the control process proceeds to step 40, and the electric power supply Ph to the heater is calculated and the result is added to the value of Phn in the memory in the same manner as in the flow chart of FIG. 7, and next in step 45 a count number N for counting the number of calculation of the electric supply to the heater is increased by 1. Then the control process proceeds to step 50, and it is checked if N is equal to 256 or not. If N is equal to 256, the process proceeds to step 60, and the value of Phn in the memory showing the sum of 256 times measurements of the electric power supply to the heater is divided by N, i.e. 256, so that the mean value Phm of the electric power supply to the heat is calculated in the same manner as in step 60 in the flow chart of FIG. 7.

If, however, it was judged in step 50 that N is not equal to 256, the control process proceeds to step 51, and it is checked if N is equal to or greater than 100 and not smaller than 256. Then, if the answer is yes, the process proceeds to step 52, and it is checked if the idle switch is on or not. If it was detected here that the idle switch is not on, it is meant that the idling condition which continued for the time being has now ended but an accumulation of data with regard to the electric power supply to the heater in a period more than 1600 ms is available. Thus, the control process proceeds to step 60, and the value of Phn in the memory is divided by the current count of N to obtain the mean value Phm. Subsequently, in step 65 N is reset to zero, and the process proceeds to step 70 so as to obtain the correction amount for the target value for the electric resistance of the heater based upon the mean value of the electric power supply to the heater in the same manner as in step 70 in the flow chart of FIG. 7.

If the answer in step 51 is no, it is meant that the number of measurements is still insufficient. If the answer in step 52 is yes, it is meant that the measurement may be continued further. Therefore, in both cases the control process proceeds toward step 80 without renewing the correction amount ΔRt for the target value for the electric resistance of the heater. By incorporating such a compromise that if the predetermined operating condition for obtaining the data for the renewal of the target value of the electric resistance of the heater continues at least 1600 ms the renewal of the target value is carried out based upon the date obtained by that time, it is avoided that the control device based upon the learning principle is made in fact ineffective because of insufficiency of the learning caused by not improbable disturbances in the normal operations of the vehicle.

Although the invention has been described with respect to some preferred embodiment thereof, it will be understood by those skilled in the art that various modifications are possible with respect to the shown embodiments without departing from the spirit of the present invention.

We claim:

1. A control device for controlling supply of electric power to a heater for an oxygen sensor for detecting oxygen in an exhaust system of an internal combustion engine for a vehicle, said control device comprising a means for detecting electric resistance of said heater and controlling said supply of electric power so as to maintain the detected electric resistance at a target value therefor, further comprising a means for detecting a predetermined operating condition of the engine, a means for detecting the amount of electric power supplied to said heater when the engine is operating at said predetermined operating condition, and a means for modifying said target value for the electric resistance of said heater so as to cancel difference between said detected value of said supply of electric power to said heater and a standard value therefor.

2. A control device according to claim 1, wherein said means for detecting the electric resistance of said heater and said means for detecting the amount of electric power supplied to said heater include a common series connection of a switching transistor and a comparing resistor connected in series with said heater, and a means for measuring a voltage across said comparing resistor, said switching transistor being controlled to be conductive according to a controlled duty factor.

3. A control device according to claim 1, wherein said means for detecting the amount of electric power supplied to said heater collects data of the amount of electric power applied to said heater cyclically for a predetermined period and determines the amount of electric power supplied to said heater as a mean value of said data.

4. A control device according to claim 1, wherein said means for detecting the amount of electric power supplied to said heater starts to detect the amount of electric power supplied to said heater when the engine is operating at said predetermined operating condition for a predetermined period.

5. A control device according to claim 1, wherein said means for detecting the amount of electric power supplied to said heater detects the amount of electric power supplied to said heater when the engine is operating at said predetermined operating condition just after the engine has been operating at a predetermined pro-operating condition.

6. A control device according to claim 5, wherein said pro-operating condition is that the vehicle has been running at a speed within a predetermined normal speed range for a predetermined period.

7. A control device according to claim 5, wherein said pro-operating condition is that the engine has been operating at load and rotational speed correlated within a predetermined mutually balanced range.

8. A control device according to claim 5, wherein said pro-operating condition is that a mean value of the amount of intake air in a predetermined period is in a predetermined medium range.

9. A control device according to claim 1, wherein said means for detecting the amount of electric power supplied to said heater collects data of the amount of electric power supplied to said heater for a period which is equal to or longer than a predetermined minimum period but is not longer than a predetermined maximum period during which the engine is operating at said predetermined operational condition, and provides the amount of electric power applied to said heater as a mean value of said data.

10. A control device according to claim 1, wherein said means for detecting a predetermined operating condition of the engine detects an idling condition thereof.

* * * * *

UNITED STATES PATENT AND TRADEMARK OFFICE
CERTIFICATE OF CORRECTION

PATENT NO. : 4,938,196
DATED : July 3, 1990
INVENTOR(S) : Kouichi HOSHI, et al

It is certified that error appears in the above-identified patent and that said Letters Patent is hereby corrected as shown below:

| Column | Line | |
|--------|------|---|
| 2 | 37 | Change "hear" to --heat--. |
| 6 | 32 | Before "is added" change "Phn" to --Ph--. |
| 9 | 53 | Change "contunuing" to --continuing--. |
| 9 | 65 | Change "measurement" to --measurements--. |
| 10 | 9 | Change "about" to --of--. |

Signed and Sealed this

Third Day of December, 1991

*Attest:*

HARRY F. MANBECK, JR.

*Attesting Officer*   *Commissioner of Patents and Trademarks*